US00PP11423P

United States Patent [19]

Austin

[11] Patent Number: Plant 11,423

[45] Date of Patent: Jun. 20, 2000

[54] SHRUB ROSE PLANT NAMED 'AUSTOP'

[75] Inventor: David C. H. Austin, Wolverhampton, United Kingdom

[73] Assignee: David Austin Roses Limited, Wolverhampton, United Kingdom

[21] Appl. No.: 09/168,199

[22] Filed: Oct. 7, 1998

[51] Int. Cl.[7] ..... A01H 5/00

[52] U.S. Cl. ..... Plt./107

[58] Field of Search ..... Plt./107, 102, 148

[56] References Cited

U.S. PATENT DOCUMENTS

| | | | |
|---|---|---|---|
| P.P. 8,814 | 7/1994 | Austin | Plt./107 |
| P.P. 8,838 | 7/1994 | Austin | Plt./107 |
| P.P. 9,010 | 12/1994 | Austin | Plt./107 |
| P.P. 9,526 | 4/1996 | Austin | Plt./107 |

*Primary Examiner*—Howard J. Locker

*Attorney, Agent, or Firm*—Klarquist Sparkman Campbell Leigh & Whinston, LLP

[57] ABSTRACT

A shrub rose plant having good disease resistance; Old rose appearance; pale pink flowers which repeat well; and Portland type leaves and flowers.

1 Drawing Sheet

The present invention relates to a new and distinct variety of shrub rose plant of the *Rosa hybrida* class which was originated by me by crossing the variety 'Fair Bianca', unpatented, with an unnamed seedling.

The primary objective of this breeding was to produce a new shrub rose variety having good disease resistance, an Old rose appearance with pale pink flowers which repeat well, and Portland type leaves and flowers. The objective was substantially achieved, along with other desirable improvements, as evidenced by the following unique combination of characteristics that are outstanding in the new variety and that distinguish it from its parents, as well as from all other varieties of which I am aware:

1. Fairly upright growth;
2. Portland type leaves and flowers;
3. Large, pale pink blooms;
4. Moderate to strong fragrance;
5. Very good disease resistance; and
6. Very good flower production.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Fair Bianca' (unpatented).

*Pollen parent.*—Unnamed seedling of unknown parentage.

Classification:

*Botanical.*—*Rosa hybrida*.

*Commerical.*—Shrub.

Flower

Observations made from specimens grown in a garden environment at Albrighton, Wolverhampton, England, Jul. 17, 1995.

Blooming habit: Recurrent.

Bud:

*Size.*—About one inch long when the petals start to unfurl.

*Form.*—The bud form is short, pointed ovoid.

*Color.*—When sepals first divide, bud color is Red Group 38B and Red Group 37B. When half blown, the upper sides of the petals are Red Group 56D, and the lower sides of the petals are Red-Group 56C and Red-Purple Group 62D.

*Sepals.*—Color: Yellow-Green Group 144B. Surface texture: Upper side hairy; underside waxy. There are three lightly appendaged sepals and two unappendaged sepals with hairy edges.

*Receptacle.*—Color: Yellow-Green Group 144B. Shape: Funnel. Size: Small (about ½ inch long×¼ inch wide). Surface: Smooth.

*Peduncle.*—Length: Medium to short, averaging about ½ to 1½ inches. Surface: Prickly. Color: Yellow-Green Group 152B and Greyed-Purple Group 184A. Strength: Erect.

Bloom:

*Size.*—Large. Average open size is three inches.

*Borne.*—Singly and several together in pyramidal clusters of two to three blooms.

*Stems.*—Normal strength. Average length is about 10 to 24 inches.

*Form.*—When first open: Bloom is flat. Permanence: Outer petals curl back.

*Petalage.*—Number of petals under normal conditions: 73.

*Color.*—The upper sides of the petals are Red Group 56C. The reverse sides of the petals are Red Group 56B. The base of each petal is Yellow Group 10D and Yellow Group 4A. The major color on the upper sides is Red Group 56C.

*Variegations.*—None.

*Discoloration.*—The general tonality at the end of the first day: Red Group 56C. At the end of the third day: Same.

*Fragrance.*—Moderate to strong. Soft, Old rose and lilac character.

Petals:

*Texture.*—Leathery.

*Shape.*—Notched.

*Form.*—Tips slightly recurved. Edges slightly quilled towards center.

*Arrangement.*—Irregular. Petaloids are few and small in the center.

*Persistence.*—Petals hang on and dry.

*Lastingnes.*—On the plant: Long, about seven days. As a cut flower: Not tested.

Reproductive parts:

*Anthers.*—Size: Medium. Quantity: Medium. Color: Yellow-Orange Group 15B. Arrangement: Partly tucked in calyx.

*Filaments.*—Color: Yellow Group 8B.

*Pollen.*—Color: Yellow-Orange Group 15A.

*Styles.*—Color: Yellow-Green Group 149D.

*Stigmas.*—Color: Yellow Group 8A.

Form: Shrub.

Growth: Upright, bushy. Mature plant is four feet in height and 2½ feet in width.

*Foliage.*—Number of leaflets on normal mid-stem leaves: Five.

*Size.*—Medium (4–6½" long×3–5" wide).

*Color.*—New foliage: Upper side: Green Group 143A. Lower side: Green Group 143C. Old foliage: Upper side: Green Group 137A. Lower side: Green Group 138A.

Leaflets:

*Shape.*—Elliptic.

*Texture.*—Upper side: Leathery, semi-glossy.

*Edge.*—Serrated.

*Serration.*—Double, medium.

*Petiole rachis.*—Color: Green Group 143C and Greyed-Red Group 182A.

*Petiole underside.*—Rough.

*Stipules.*—Medium, about one inch long.

*Disease resistance.*—Resistant to mildew, blackspot and rust under normal growing conditions at Albrighton, Wolverhampton, England.

Wood:

*New wood.*—Color: Yellow-Green Group 146A and Greyed-Purple Group 183B. Bark: Rough.

*Old wood.*—Color: Yellow-Green Group 144A. Bark: Rough.

Prickles:

*Quantity.*—On main canes from base: Ordinary. On laterals from main canes: Few.

*Position.*—Quite evenly up the stems.

*Form.*—Short, hooked downward.

*Color when young.*—Greyed-Orange Group 164B.

*Color when mature.*—Greyed-Orange Group 164B.

Small prickles:

*Quantity.*—On main stalks: Few. On laterals: Many.

*Color.*—Greyed-Orange Group 164B.

I claim:

1. A new and distinct variety of shrub rose plant of the *Rosa hybrida* class, substantially as herein shown and described, characterized particularly as to novelty by the unique combination of its good disease resistance; Old rose appearance; pale pink flowers which repeat well; and Portland type leaves and flowers.

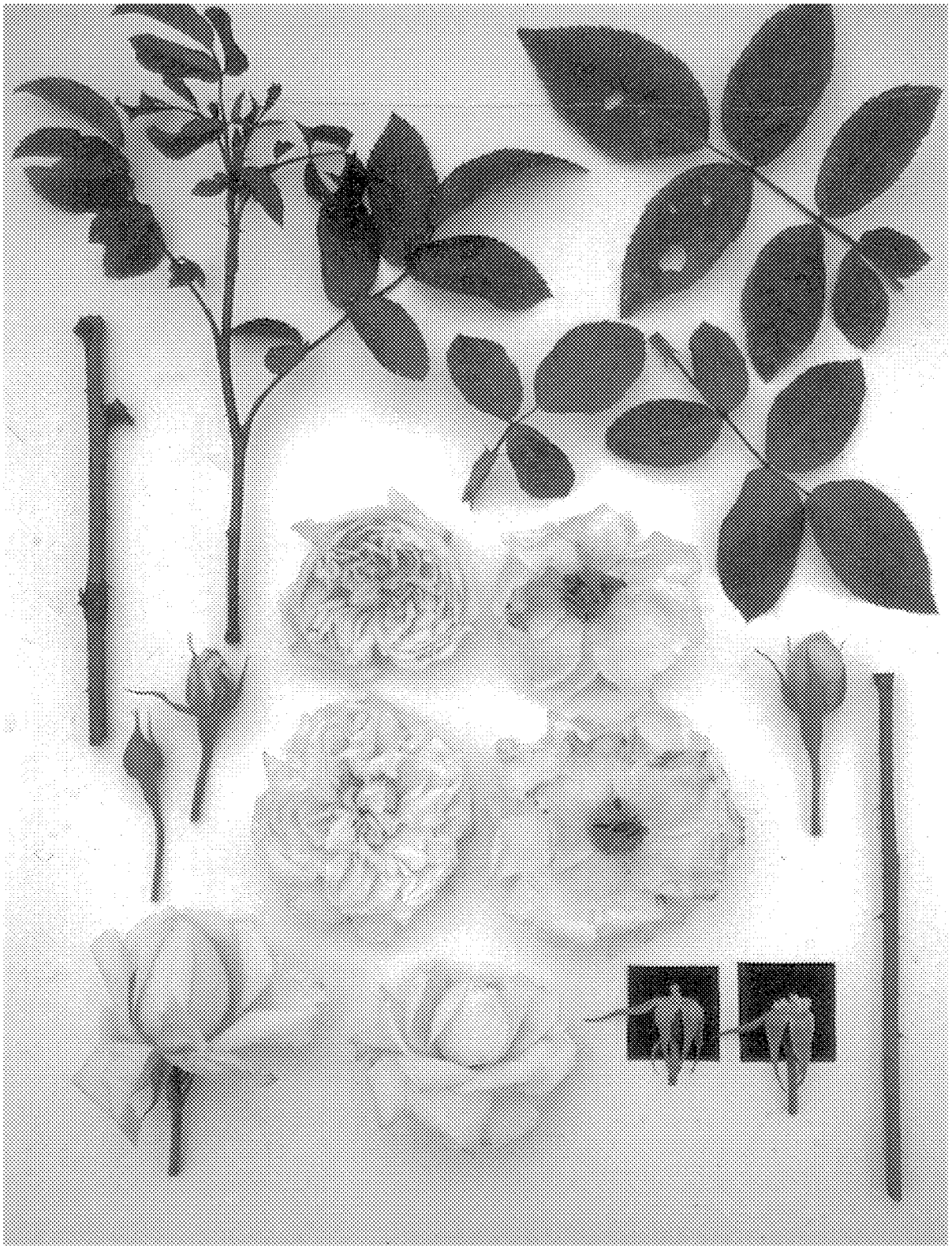

* * * * *